(12) United States Patent
Chang (10) Patent No.: US 10,561,331 B2
(45) Date of Patent: Feb. 18, 2020

(54) METHOD AND APPARATUS FOR DETECTING ATRIAL FIBRILLATION

(71) Applicant: Kuo-Yuan Chang, Taipei (TW)

(72) Inventor: Kuo-Yuan Chang, Taipei (TW)

(*) Notice: Subject to any disclaimer, the term of this patent is extended or adjusted under 35 U.S.C. 154(b) by 260 days.

(21) Appl. No.: 15/839,289

(22) Filed: Dec. 12, 2017

(65) Prior Publication Data
US 2018/0160926 A1 Jun. 14, 2018

(30) Foreign Application Priority Data
Dec. 12, 2016 (TW) .............................. 105141103 A (51) Int. Cl.
| | |
|---|---|
| *A61B 5/15* | (2006.01) |
| *A61B 5/00* | (2006.01) |
| *A61B 5/0205* | (2006.01) |
| *A61B 5/046* | (2006.01) |
| *A61B 5/024* | (2006.01) |
| *A61B 5/025* | (2006.01) |
| *A61B 5/0402* | (2006.01) |

(52) U.S. Cl.
CPC .............. *A61B 5/046* (2013.01); *A61B 5/025* (2013.01); *A61B 5/02405* (2013.01); *A61B 5/02422* (2013.01); *A61B 5/7257* (2013.01); *A61B 5/7264* (2013.01); *A61B 5/02438* (2013.01); *A61B 5/04023* (2013.01)

(58) Field of Classification Search
None
See application file for complete search history.

(56) References Cited

U.S. PATENT DOCUMENTS

| | | | | |
|---|---|---|---|---|
| 5,609,158 | A | * | 3/1997 | Chan .................... A61B 5/0464 600/518 |
| 8,010,347 | B2 | * | 8/2011 | Ricci .................. G06K 9/00523 600/509 |
| 2014/0027464 | A1 | * | 1/2014 | Huang .................... A47K 10/38 221/45 |
| 2016/0087603 | A1 | * | 3/2016 | Ricci .................. G06K 9/00523 702/19 |

* cited by examiner

Primary Examiner — Brian T Gedeon
(74) Attorney, Agent, or Firm — Muncy, Geissler, Olds & Lowe, P.C.

(57) ABSTRACT

A method of detecting atrial fibrillation includes detecting a pulse signal to obtain a time pulse waveform and converting it to an energy spectrum waveform via Fast Fourier Transform. The energy spectrum waveform includes a first frequency region, a second frequency region, and a third frequency region. The number of spikes in each frequency region was calculated and the heart indexes of the first, second, and third frequency regions were obtained, which were the first heart index, the second heart index, and the third heart index. And by the sum of the three heart index values and the first heart index to determine the possibility of atrial fibrillation. An apparatus for detecting atrial fibrillation is also provided, whereby the user can determine the possibility and predicting atrial fibrillation by simple measurement of blood pressure at home.

18 Claims, 13 Drawing Sheets

METHOD AND APPARATUS FOR DETECTING ATRIAL FIBRILLATION

BACKGROUND OF THE INVENTION

1. Field of the Invention

The present invention relates to a biomedical electronic technology, particularly to a method and apparatus for detecting atrial fibrillation.

2. Description of the Prior Art

Atrial fibrillation (Af) is a disease frequently seen in clinic among the cardiac arrhythmia diseases. The incidence rate of atrial fibrillation linearly increases with age. The risk of apoplexy of an Af patient is 4-5 times that of an ordinary person. At present, cardiac arrhythmia is usually diagnosed with the 12-lead electrocardiography and the treadmill electrocardiography. The electrocardiography can record the seizures of cardiac arrhythmia and thus can apply to determine the classification and severity of cardiac arrhythmia. Therefore, electrocardiography can be used to diagnose most patients of atrial fibrillation. However, electrocardiography must be undertaken in a professional hospital and interpreted by a professional physician. Users are unlikely to perform electrocardiography at home. Therefore, users cannot enjoy the benefit of electrocardiography conveniently.

SUMMARY OF THE INVENTION

One objective of the present invention is to provide an atrial fibrillation detection method to determine the possibility of atrial fibrillation and realize prediagnosis of atrial fibrillation, whereby to solve the abovementioned problems.

Another objective of the present invention is to provide an atrial fibrillation detection apparatus, whereby the user can determine the possibility of atrial fibrillation and realize pre-diagnosis of atrial fibrillation at home via simple blood pressure measurement. Once pre-diagnosed to have the possibility of atrial fibrillation, the patient is sent to a hospital for definite diagnosis and then treated professionally by physicians, whereby to prevent from apoplexy induced by atrial fibrillation.

In order to achieve the abovementioned objectives, one embodiment of the present invention proposes an atrial fibrillation detection method, which comprises steps: detecting a pulse signal to obtain a time pulse waveform; and converting the time pulse waveform into an energy spectrum waveform via Fast Fourier Transform (FFT), wherein the energy spectrum waveform includes at least three frequency regions, which are respectively a first frequency region, a second frequency region and a third frequency region, and wherein three frequency regions respectively have three primary amplitudes, which are a first primary amplitude, a second primary amplitude and a third primary amplitude; calculating the number of the peaks of noise in each frequency region and defining the number of the peaks as a heart index, wherein the heart indexes of the first, second, and third frequency regions are respectively a first heart index, a second heart index and a third heart index, and wherein the primary amplitude of each frequency region is multiplied by a proportional coefficient to function as a benchmark value in the frequency region, and wherein the noise signals in each frequency region, which have an intensity higher than the benchmark value, are regarded as the peaks in the frequency region; using the sum of the first, second and third heart indexes as a judgement index and determining that there is possibility of atrial fibrillation while the judgement index is equal to or greater than a first standard value and the first heart index is equal to or greater than a second standard, wherein the determination of the first standard value and the second standard value correlates with the determination of the proportional coefficient.

One embodiment of the present invention proposes an atrial fibrillation detection apparatus, which comprises an inflatable cuff wrapped around the arm of the testee and inflated to pressurize the arm and sense a pulse signal; a host device having a transducer thereinside, connected with the inflatable cuff through an air hose, and controlling the operation modes of the inflatable cuff to acquire corresponding pulse signals; a first module acquiring the time pulse waveform of the pulse signal of the testee within a special time interval; a second module converting the time pulse waveform into an energy spectrum waveform through Fast Fourier Transform, wherein the energy spectrum waveform includes at three frequency regions, which are respectively a first frequency region, a second frequency region and a third frequency region, and wherein three frequency regions respectively three primary amplitudes, which are a first primary amplitude, a second primary amplitude and a third primary amplitude; a third module calculating the number of the peaks of noise in each frequency region and defining the number of the peaks in each frequency region as a heart index in the frequency region, wherein the heart indexes of the first, second, and third frequency regions are respectively a first heart index, a second heart index and a third heart index, and wherein the primary amplitude of each frequency region is multiplied by a proportional coefficient to function as a benchmark value in the frequency region, and wherein the noise signals in each frequency region, which have an intensity higher than the benchmark value, are regarded as the peaks in the frequency region; and a display module presenting the three heart indexes of the three frequency regions, wherein the sum of the three heart indexes and the first heart index are used to determine whether there is possibility of atrial fibrillation.

BRIEF DESCRIPTION OF THE DRAWINGS

FIG. 7b shows an energy spectrum waveform corresponding to the time pulse waveform in FIG. 7a;

FIG. 8b shows an energy spectrum waveform corresponding to the time pulse waveform in FIG. 8a;

FIG. 9b shows an energy spectrum waveform corresponding to the time pulse waveform in FIG. 9a;

FIG. 10b shows an energy spectrum waveform corresponding to the time pulse waveform in FIG. 10a;

FIG. 11b shows an energy spectrum waveform corresponding to the time pulse waveform in FIG. 11a;

DESCRIPTION OF THE PREFERRED EMBODIMENTS

Figure 1:
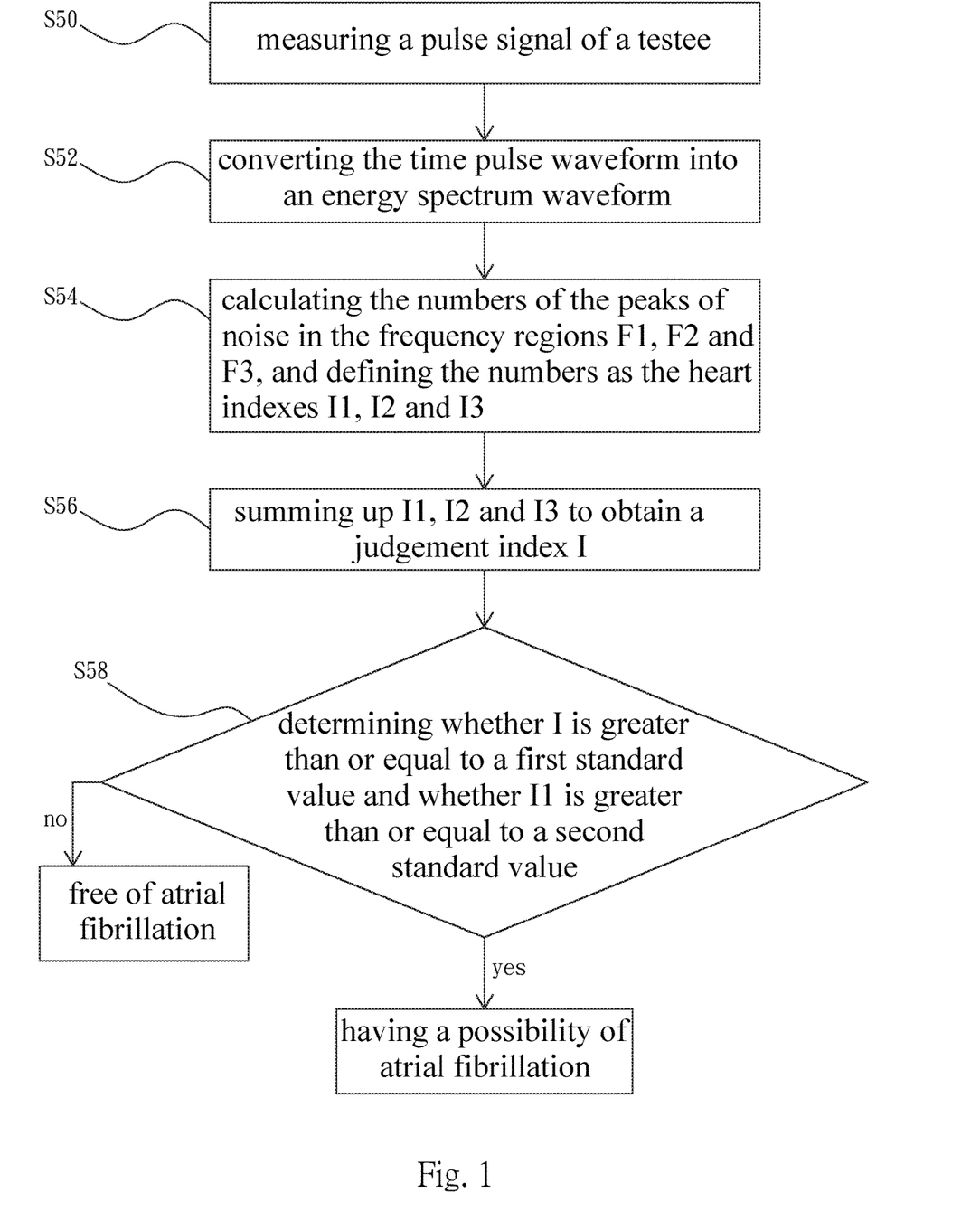
FIG. 1 is a flowchart of an atrial fibrillation detection method according to one embodiment of the present invention.

Refer to FIG. 1 a flowchart of an atrial fibrillation detection method according to one embodiment of the present invention. In this embodiment, the method of the present invention comprises Steps S50-S58. In Step S50, detect a pulse signal to obtain a time pulse waveform. In Step S52, convert the time pulse waveform into an energy spectrum waveform via Fast Fourier Transform (FFT). The energy spectrum waveform includes at least three frequency regions, which are respectively a first frequency region F1, a second frequency region F2 and a third frequency region F3. Each frequency region has a primary amplitude. In Step S54, calculate the number of the peaks of noise in each frequency region. The number of the peaks in each frequency region is defined as a heart index of the frequency region, wherein the heart indexes of the first, second, and third frequency regions are respectively a first heart index, a second heart index and a third heart index. The primary amplitude of each frequency region is multiplied by a proportional coefficient to function as a benchmark value in the frequency region. The peaks in each frequency region, which have an intensity higher than the benchmark value, are regarded as noise signals in the frequency region. In one embodiment, a first heart index I1 is defined by the total number of the noise peaks in the first frequency region F1; a second heart index I2 is defined by the total number of the noise peaks in the second frequency region F2; a third heart index I3 is defined by the total number of the noise peaks in the third frequency region F3. The sum of the first heart index I1, the second heart index I2 and the third heart index I3 as well as the first heart index I1 are used to determine whether there is possibility of atrial fibrillation. The abovementioned process includes Step S56 and Step S58. In Step S56, calculate the sum of the first heart index I1, the second heart index I2 and the third heart index I3 to obtain a judgement index I. In Step S58, determine whether the judgement index I is greater than or equal to a first standard value and whether the first heart index I1 is greater than or equal to a second standard value. If the judgement index I is greater than or equal to the first standard value and the first heart index I1 is greater than or equal to the second standard value, there is possibility of atrial fibrillation. If the judgement index I is smaller than the first standard value and/or the first heart index I1 is smaller than the second standard value, there is no possibility of atrial fibrillation. The determination of the standard values correlates with the determination of the proportional coefficient.

In one embodiment, the first frequency region F1 is a region of ±0.5 times a first master frequency of the heartbeat frequency; the second frequency region F2 is a region of ±0.5 times a second master frequency of the heartbeat frequency; the third frequency region F3 is a region of ±0.5 times a third master frequency of the heartbeat frequency. For example, the heartbeat frequency of a person is 60 cycles/minute. Thus, the first frequency region F1 is 30-90 cycles/minute; the second frequency region F2 is 90-150 cycles/minute; the third frequency region F3 is 150-210 cycles/minute. The first frequency region F1, the second frequency region F2 and the third frequency region F3 respectively have a first primary amplitude A1, a second primary amplitude A2 and a third primary amplitude A3. The products of the first primary amplitude A1, the second primary amplitude A2 and the third primary amplitude A3 respectively multiplied by a proportional coefficient separately function as the benchmark values for verifying noise in the first frequency region F1, the second frequency region F2 and the third frequency region F3. In one embodiment, the proportional coefficient is 5; the first standard value is 2, and the second standard value is 5. However, the present invention is not limited by the abovementioned embodiment. The abovementioned values may vary with the FFT parameters. For an ordinary testee who is free of cardiac arrhythmia, the first heart index I1, the second heart index I2 and the third heart index I3 are all equal to zero. Therefore, if I1+I2+I3≥5 and I1≥2 for a testee, the testee will be determined to have the possibility of atrial fibrillation.

Figure 2:
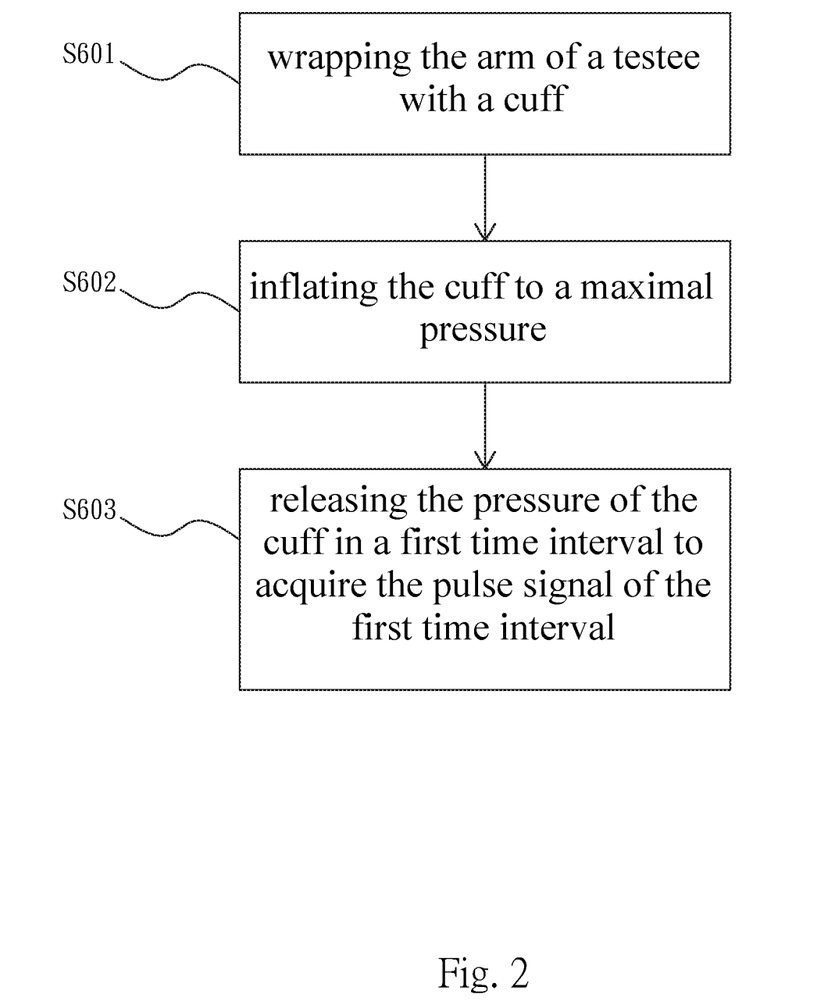
FIG. 2 is a flowchart of a method for measuring a pulse signal of a testee according to one embodiment of the present invention.

Refer to FIG. 2. In one embodiment, the step of detecting the pulse signal (Step S50) further includes Steps S601-S603. In Step S601, wrap the arm of a testee with an inflatable cuff. In Step S602, inflate the cuff to a maximal pressure. In Step S603, release the pressure of the cuff in a first time interval to acquire the pulse signal of the first time interval. In one embodiment, the pressure release rate of the cuff in the first time interval is 2-7 mmHg/sec.

Figure 3:
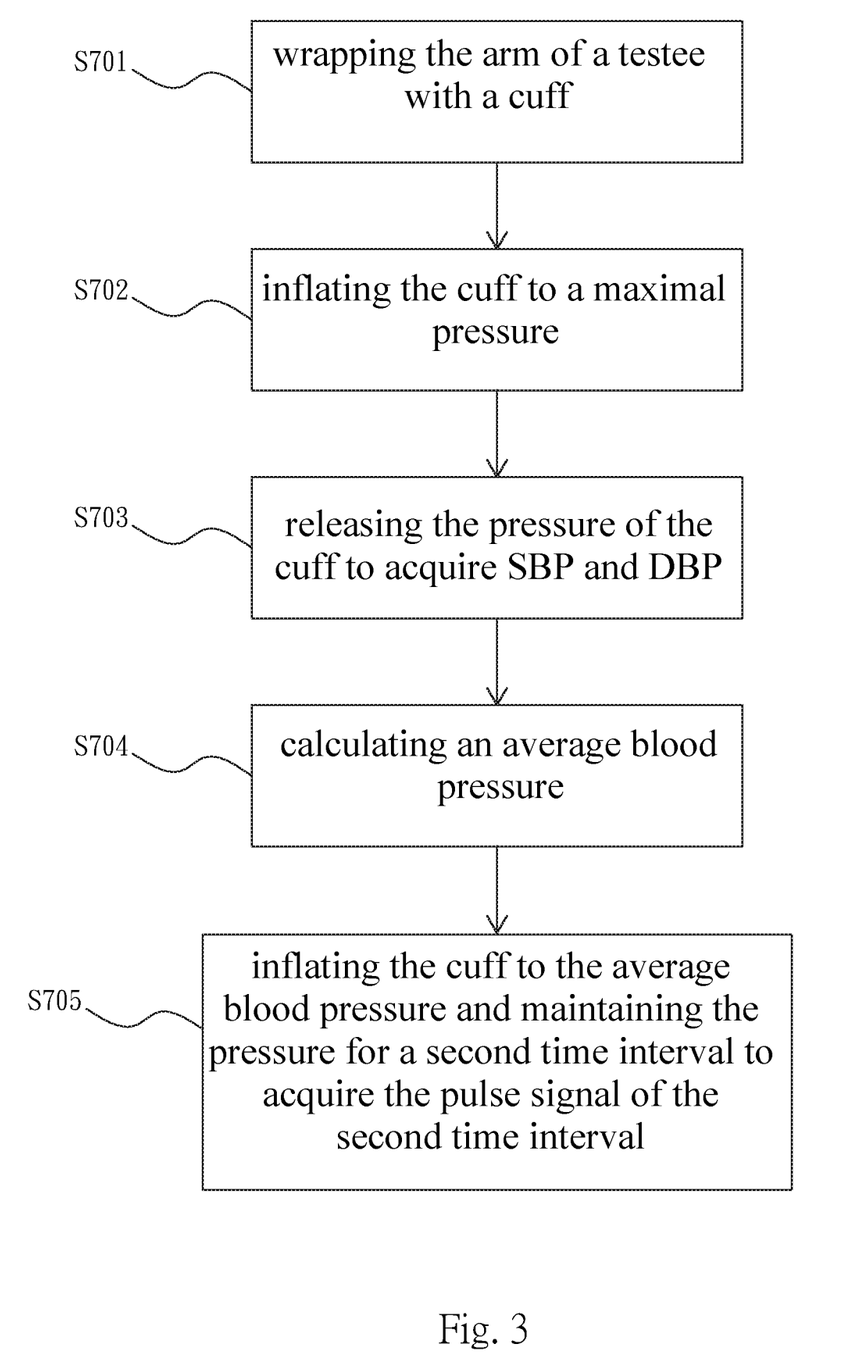
FIG. 3 is a flowchart of a method for measuring a pulse signal of a testee according to another embodiment of the present invention.

Refer to FIG. 3. In one embodiment, the step of detecting the pulse signal (Step S50) further includes Steps S701-S705. In Step S701, wrap the arm of a testee with an inflatable cuff. In Step S702, inflate the cuff to a maximal pressure. In Step S703, release the pressure of the cuff to calculate a systolic blood pressure (SBP) and a diastolic blood pressure (DBP). In Step S704, calculate an average blood pressure BPav. The equation for calculating the average blood pressure is BPav=1/3·SBP+2/3·DBP. In Step S705, inflate the cuff to the average blood pressure and maintain the pressure for a second time interval to acquire the pulse signal of the second time interval.

Figure 4:
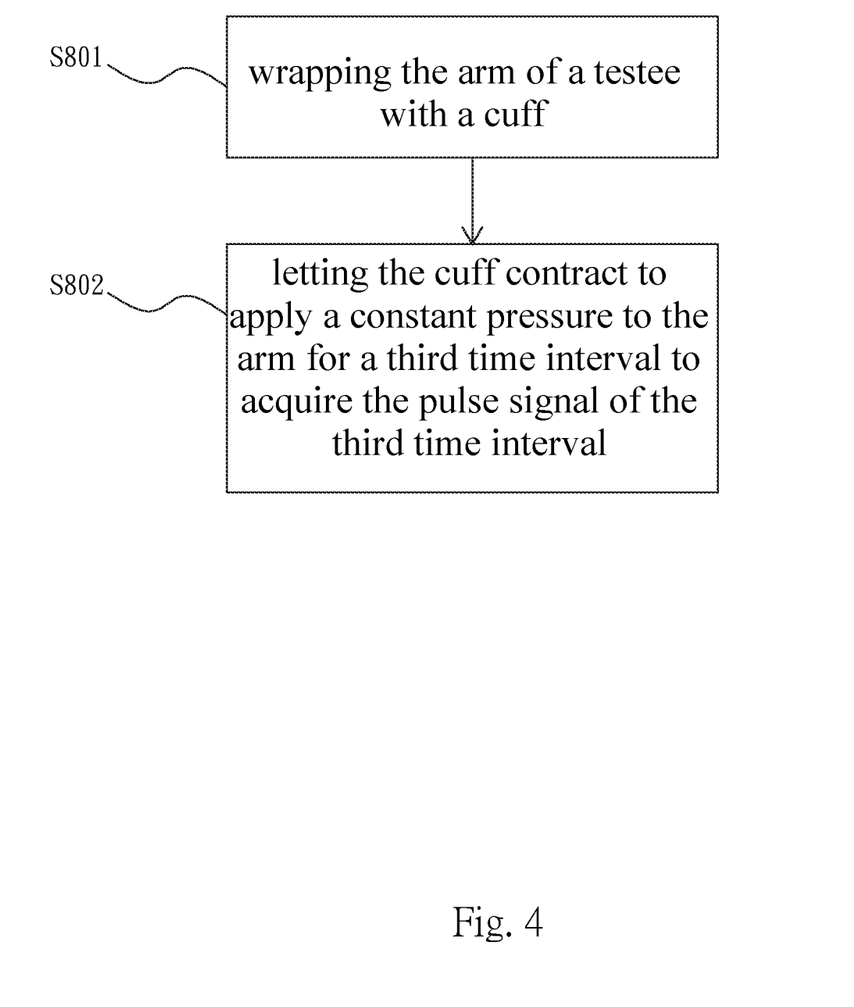
FIG. 4 is a flowchart of a method for measuring a pulse signal of a testee according to yet another embodiment of the present invention.

Refer to FIG. 4. In one embodiment, the step of detecting the pulse signal (Step S50) further includes Step S801 and Step S802. In Step S801, wrap the arm of a testee with an inflatable cuff. In Step S802, let the cuff contract to apply a constant pressure to the arm for a third time interval to acquire the pulse signal of the third time interval. In one embodiment, the constant pressure is 50 mmHg, 60 mmHg, or 70 mmHg, or within a range of 40-70 mmHg.

In addition to the blood pressure measurement device, the pulse signal may also be obtained via a blood oxygen measurement device, an electrocardiographic measurement device, an infrared measurement device, or a heart rate measurement device.

In one embodiment, the atrial fibrillation detection method of the present invention further comprises a step: transmitting one or both of the time pulse waveform and the energy spectrum waveform to a cloud server to enable the data to be displayed, calculated, or analyzed with big data in a far end. In one embodiment, the cloud server converts the time pulse waveform into an energy spectrum waveform via FFT and calculates the heart indexes. Via uploading the time pulse waveform and/or the energy spectrum waveform to a cloud server, and/or letting the cloud server generate the energy spectrum waveform, the medical personnel can view the complete time pulse waveform and/or the complete energy spectrum waveform. Thus is realized the target of far-end healthcare.

Figure 5:
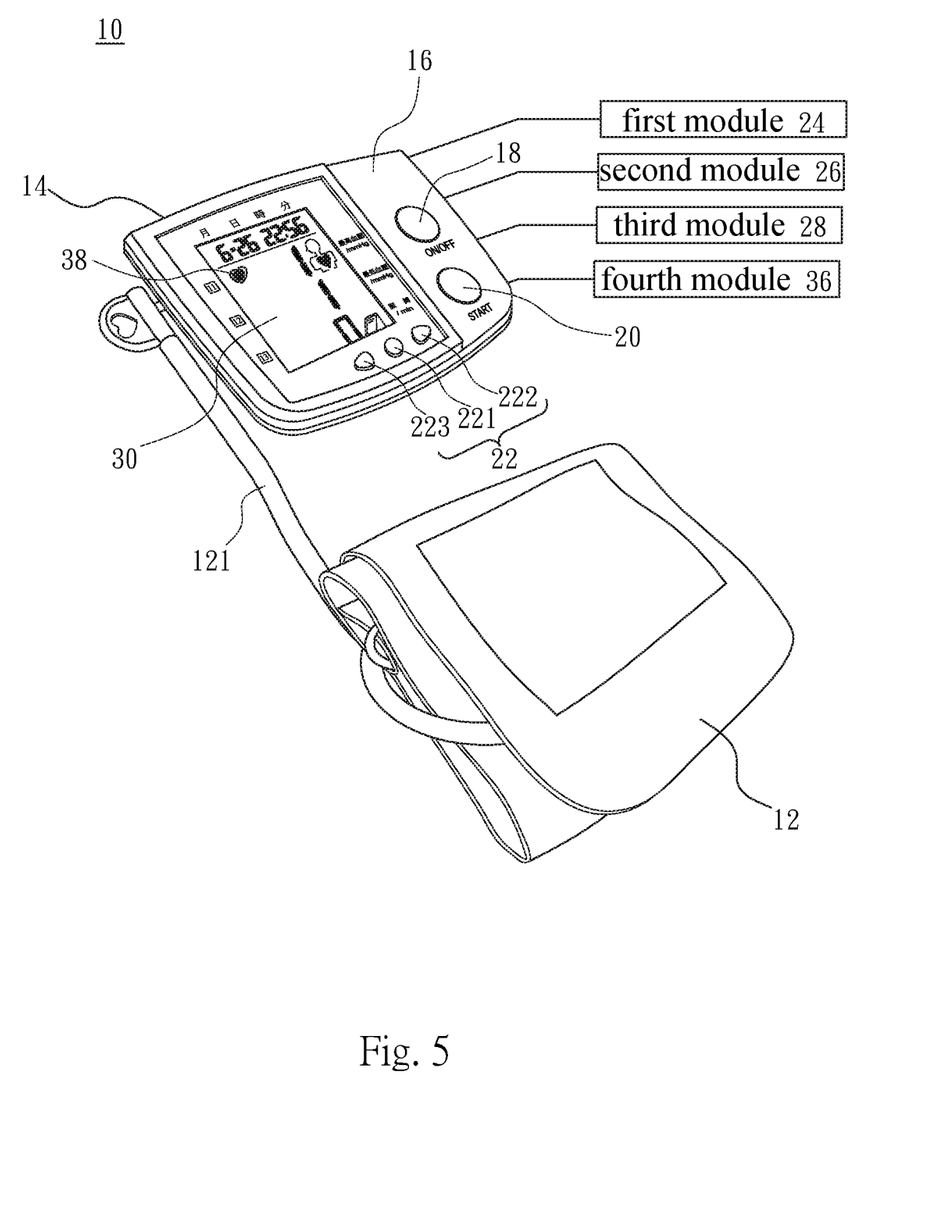
FIG. 5 is a diagram schematically showing the structure of an atrial fibrillation detection apparatus according to one embodiment of the present invention.

Refer to FIG. 5 a diagram schematically showing the structure of an atrial fibrillation detection apparatus according to one embodiment of the present invention. The atrial fibrillation detection apparatus 10 of the present invention comprises a cuff 12 used to measure blood pressure, wrapping the arm of a testee, and varying in pressure in response to the variation of the blood pressure of the blood vessels of the arm; and a host device 14 connected with the cuff 12 through an air hose 121 and controlling the operation of the cuff 12. The host device 14 includes a casing 16. The upper surface of the casing 16 has a power switch 18, a start button 20 and several function keys 22. The casing 16 includes at least one control chip (not shown in the drawing) thereinside. The control chip includes a transducer sensing the pressure variation of the cuff 12 through the air hose 121, to acquire a pulse signal, wherein the pressure variation of the cuff 12 is induced by the variation of the blood pressure.

The atrial fibrillation detection apparatus 10 of the present invention further comprises a first module 24, a second module 26, a third module 28, and a display module 30. The first module 24 acquires the time pulse waveform of the pulse signal of the testee within a special time interval. The second module 26 converts the time pulse waveform into an energy spectrum waveform through Fast Fourier Transform. The energy spectrum waveform includes at three frequency regions, which are respectively a first frequency region F1, a second frequency region F2 and a third frequency region F3. Each frequency region has a primary amplitude. For example, the first frequency region F1, the second frequency region F2 and the third frequency region F3 respectively have a first primary amplitude A1, a second primary amplitude A2 and a third primary amplitude A3. The third module 28 calculates the number of the peaks of noise in each frequency region and defines the number of the peaks in each frequency region as a heart index in the frequency region. For example, the heart indexes of the first frequency region F1, the second frequency region F2 and the third frequency region F3 are respectively a first heart index I1, a second heart index I2 and a third heart index I3. Whether a signal in a frequency region is a noise signal is determined according to a benchmark value generated via multiplying the primary amplitude of the frequency region by a proportional coefficient. The display module 30 presents the first heart index I1, the second heart index I2 and the third heart index I3. Whether there is possibility of atrial fibrillation is determined according to whether the sum of the first heart index I1, the second heart index I2 and the third heart index I3 is greater than or equal to a first standard value and whether the first heart index I1 is greater than or equal to a second standard value. In one embodiment, the proportional coefficient is 1/20; the first standard value is 5; the second standard value is 2. However, the present invention is not limited by the abovementioned embodiment. The abovementioned values may vary with the FFT parameters.

In one embodiment, the first heart index I1, the second heart index I2 and the third heart index I3 are summed up manually. In one embodiment, the atrial fibrillation detection apparatus 10 of the present invention further comprises a fourth module 36, which can sum up the first heart index I1, the second heart index I2 and the third heart index I3 to obtain a judgement index and shows the judgement index on the display module 30. In one embodiment, when the judgement index is between zero and the first standard value, an alert symbol 38 is presented on the display device 30. When the judgement index is greater than or equal to the first standard value and the first heart index I1 is greater than or equal to the second standard value, the alert symbol 38 is flashing to remind the testee of the possibility of atrial fibrillation. In one embodiment, the atrial fibrillation detection apparatus 10 of the present invention further comprises a buzzer emitting sounds to wan the testee of the possibility of atrial fibrillation.

In one embodiment, three measurement modes are built in the atrial fibrillation detection apparatus 10 of the present invention. The user may operate the function keys 22 to select the measure mode.

Figure 6A:
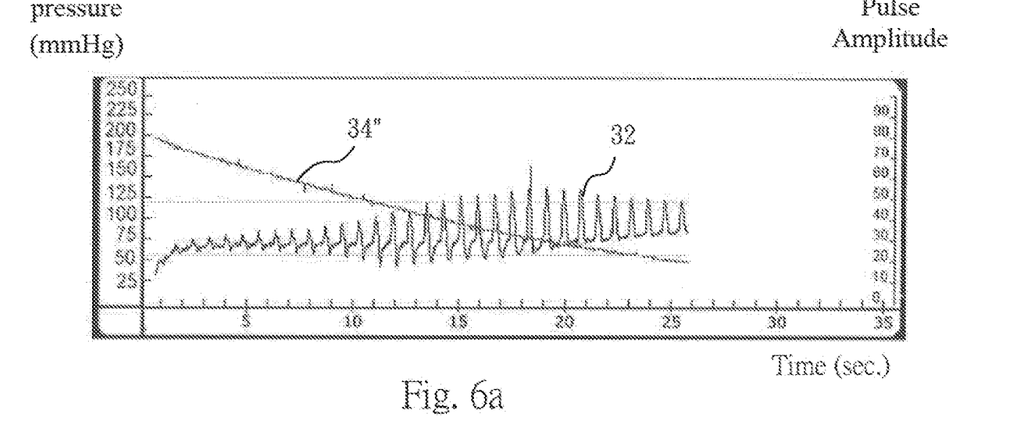
FIG. 6*a* shows a time pulse waveform detected in a testee free of cardiac arrhythmia and by an atrial fibrillation detection apparatus in a first measurement mode according to one embodiment of the present invention.
Figure 7A:
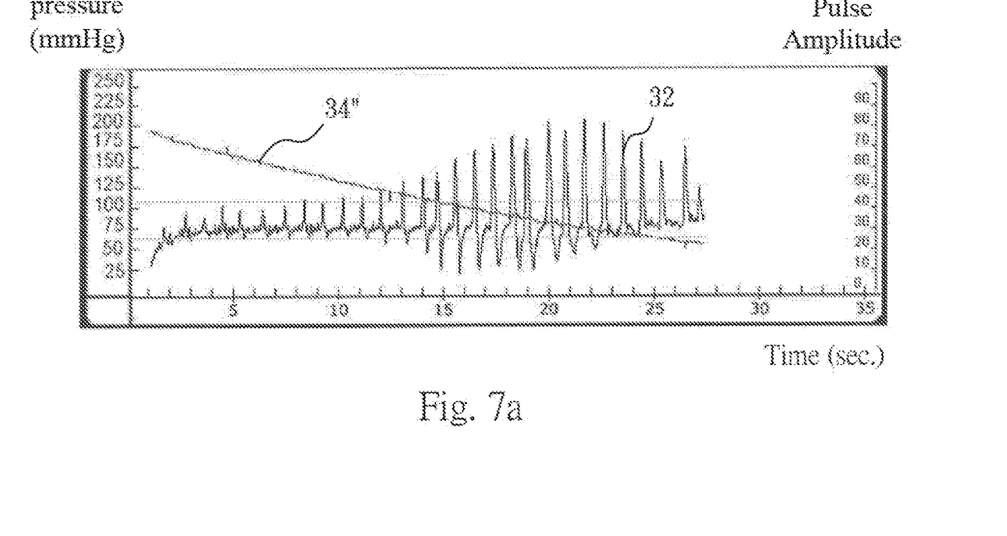
FIG. 7*a* shows a time pulse waveform detected in a testee having a possibility of atrial fibrillation and by an atrial fibrillation detection apparatus in the first measurement mode according to one embodiment of the present invention.

In a first measurement mode, the cuff 12 is inflated to a maximal pressure; the pressure of the cuff 12 is released in a first time interval; the first module 24 acquires a pulse signal 32 of the testee in the first time interval. FIG. 6a shows a time pulse waveform of a testee free of cardiac arrhythmia, wherein the time pulse waveform is measured with the cuff in a pressure-released state. FIG. 7a shows a time pulse waveform of a testee possibly suffering atrial fibrillation, wherein the time pulse waveform is measured with the cuff in a pressure-released state. In FIG. 6a and FIG. 7a, the horizontal axis denotes time; the left vertical axis denotes pressure in a unit of mmHg; the right vertical axis denotes the pulse amplitude. In addition to the pulse signal 32, each of FIG. 6a and FIG. 7a also shows a pressure curve 34", which indicates that the pressure the cuff 12 applies to the arm becomes smaller and smaller with time. In one embodiment, the pressure release rate of the cuff 12 is 2-7 mmHg/sec.

Figure 6B:
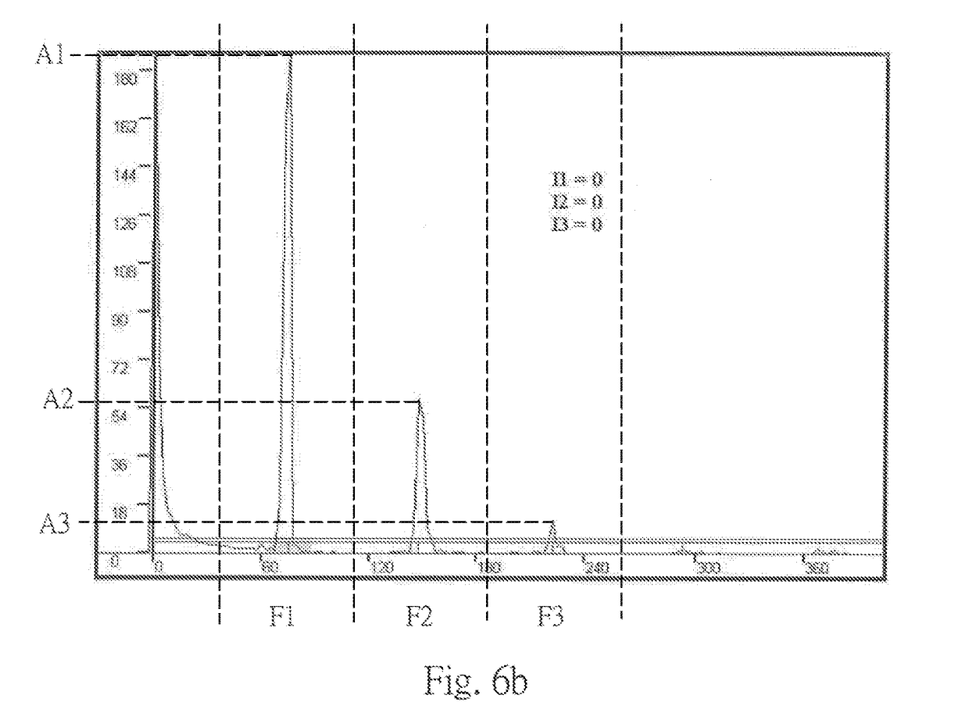
FIG. 6*b* shows an energy spectrum waveform corresponding to the time pulse waveform in FIG. 6*a*.
Figure 7B:
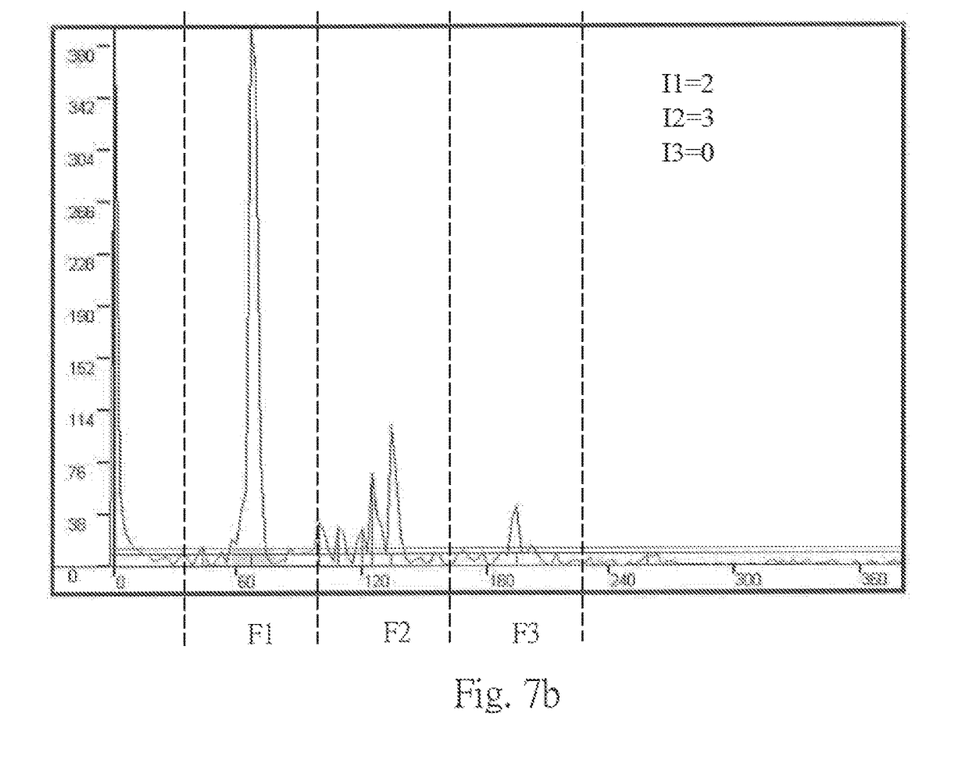

FIG. 6b and FIG. 7b respectively show the energy spectrum waveforms of the pulse signals in FIG. 6a and FIG. 7a, wherein the horizontal axis denotes the frequency and the vertical axis denotes the energy index (amplitude). The second module converts the time pulse waveform into the energy spectrum waveform through FFT, and the frequency axis of the energy spectrum waveform includes the first frequency region F1, the second frequency region F2 and the third frequency region F3. Suppose that the proportional coefficient is 1/20. Hence, the first standard value is 5, and the second standard value is 2. Refer to FIG. 6b again. The first heart index I1, the second heart index I2 and the third heart index I3 of an ordinary testee free of cardiac arrhythmia are all zero. In FIG. 7b, the first heart index I1, the second heart index I2 and the third heart index I3 are respectively 2, 3, and 0. Thus, I1+I2+I3≥5 and I1≥2. Therefore, the testee of FIG. 7a and FIG. 7b is determined to have the possibility of atrial fibrillation.

In a second measurement mode, the cuff 12 is inflated to a maximal pressure to oppress the brachial artery; while the blood circulation therein is stopped, the transducer detects the heartbeat-induced variation of the blood vessel pressure to calculate the systolic blood pressure (SBP) and the diastolic blood pressure (DBP); the systolic blood pressure (SBP) and the diastolic blood pressure (DBP) are used to calculate an average blood pressure BPav according to an equation: BPav=1/3·SBP+2/3·DBP; the cuff is then inflated to the average blood pressure and maintain the pressure for a second time interval to acquire the pulse signal of the second time interval. The second module 26 acquires the pulse signal in the second time interval. The pulse time waveforms of the blood pressure variation detected by the transducer in the second time interval are respectively shown in FIG. 8a and FIG. 9a, wherein the constant pressure of the average blood pressure, which is denoted by the pressure curve 34", is applied to the arms by the cuff 12.

Figure 8A:
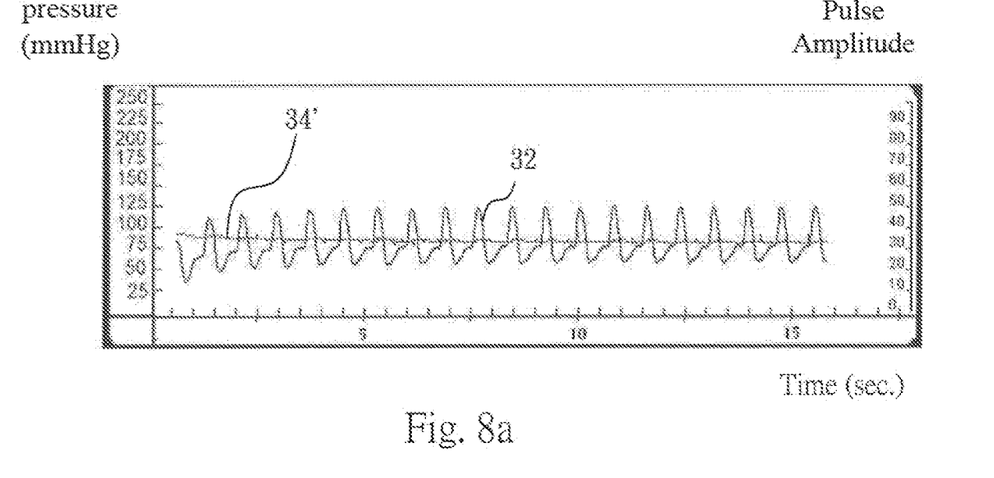
FIG. 8a shows a time pulse waveform detected in a testee free of cardiac arrhythmia and by an atrial fibrillation detection apparatus in a second measurement mode according to one embodiment of the present invention.
Figure 8B:
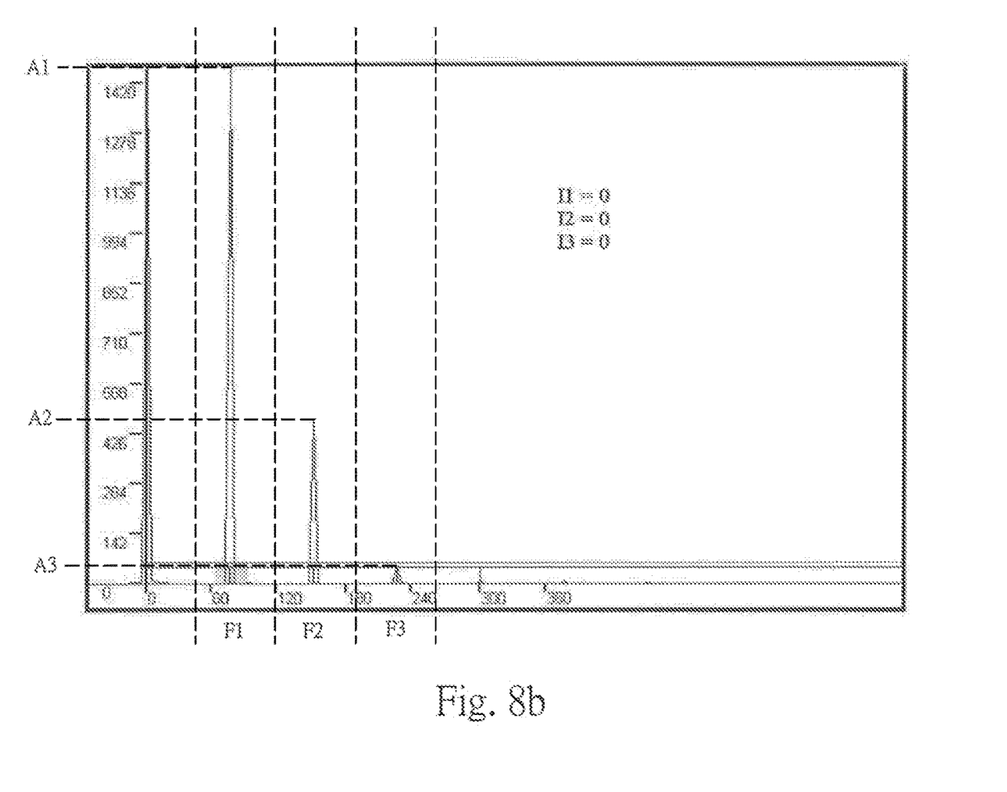
Figure 9A:
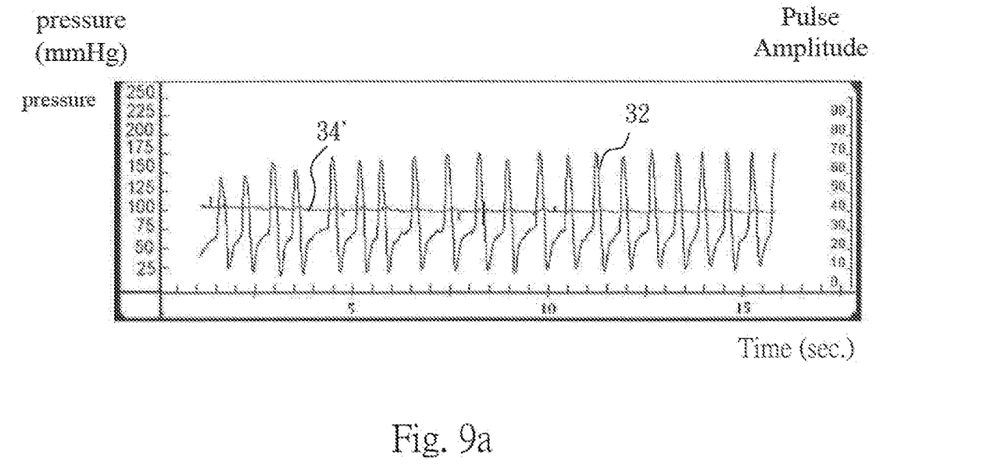
FIG. 9a shows a time pulse waveform detected in a testee having a possibility of atrial fibrillation and by an atrial fibrillation detection apparatus in the second measurement mode according to one embodiment of the present invention.
Figure 9B:
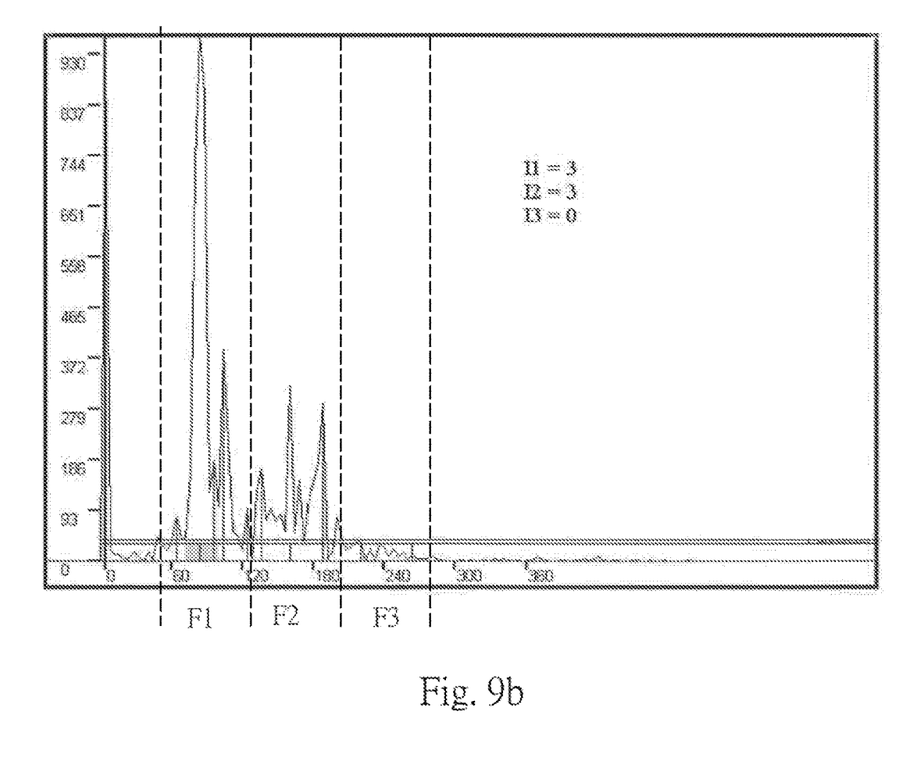

FIG. 8b and FIG. 9b respectively the energy spectrum waveforms of the pulse signals 32 in FIG. 8a and FIG. 9a, wherein the horizontal axis denotes the frequency and the vertical axis denotes the energy index (amplitude). The second module converts the time pulse waveform into the energy spectrum waveform through FFT, and the frequency axis of the energy spectrum waveform includes the first frequency region F1, the second frequency region F2 and the third frequency region F3. Suppose that the proportional coefficient is 1/20. Hence, the first standard value is 5, and the second standard value is 2. Refer to FIG. 8b again. The first heart index I1, the second heart index I2 and the third heart index I3 of an ordinary testee free of cardiac arrhythmia are all zero. In FIG. 9b, the first heart index I1, the second heart index I2 and the third heart index I3 are respectively 3, 3, and 0. Thus, I1+I2+I3≥5 and I1≥2. Therefore, the testee of FIG. 9a and FIG. 9b is determined to have the possibility of atrial fibrillation.

Figure 10A:
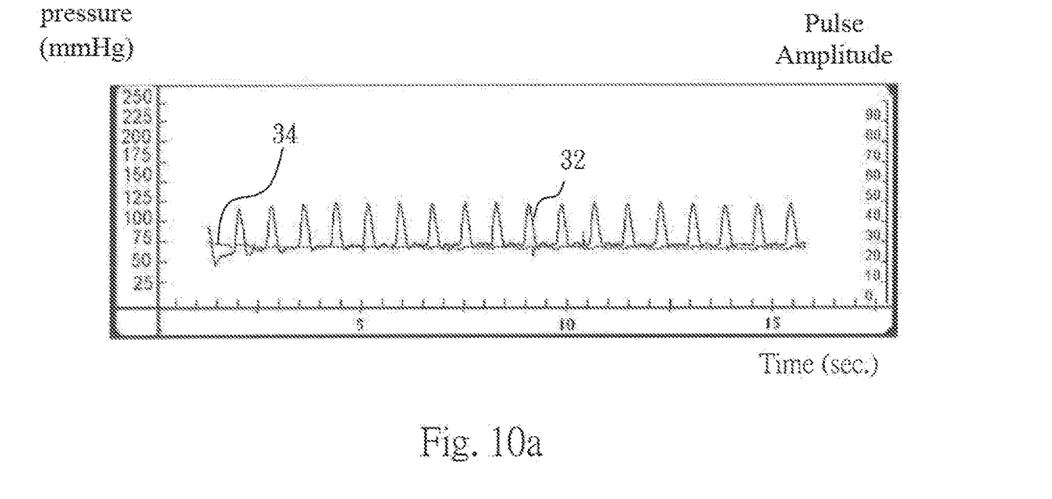
FIG. 10a shows a time pulse waveform detected in a testee free of cardiac arrhythmia and by an atrial fibrillation detection apparatus in a third measurement mode according to one embodiment of the present invention.
Figure 11A:
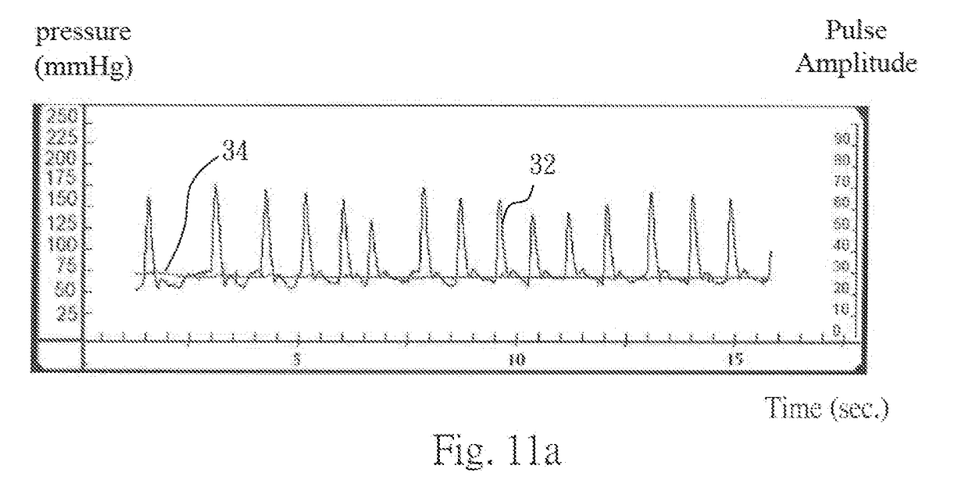
FIG. 11a shows a time pulse waveform detected in a testee having a possibility of atrial fibrillation and by an atrial fibrillation detection apparatus in the third measurement mode according to one embodiment of the present invention.

In a third measurement mode, the cuff 12 is contracted to apply a constant pressure to the arm for a first time interval, wherein the constant pressure 50 mmHg, 60 mmHg, 70 mmHg, or a pressure within the abovementioned pressures, and wherein the first time interval is 15 seconds, 20 seconds, 25 seconds, or a time interval between the abovementioned time intervals; the first module 24 acquires the time pulse waveform of the pulse signal of the testee in the first time interval; the second module 26 converts the time pulse waveform into the energy spectrum waveform through FFT. FIG. 10a shows the time pulse waveform of a testee free of cardiac arrhythmia in the third measurement undertaken by the atrial fibrillation detection apparatus 10 of the present invention. FIG. 11a shows the time pulse waveform of a testee possibly having atrial fibrillation. In FIG. 1a and FIG. 11a, the horizontal axis denotes time; the left vertical axis denotes the pressure provided by the cuff 12 in a unit of mmHg; the right vertical axis denotes the pulse amplitude. In addition to the pulse signals 32, FIG. 10a and FIG. 11a also show the pressure curves 34 of the constant pressure of 70 mmHg provided by the cuff 12.

Figure 10B:
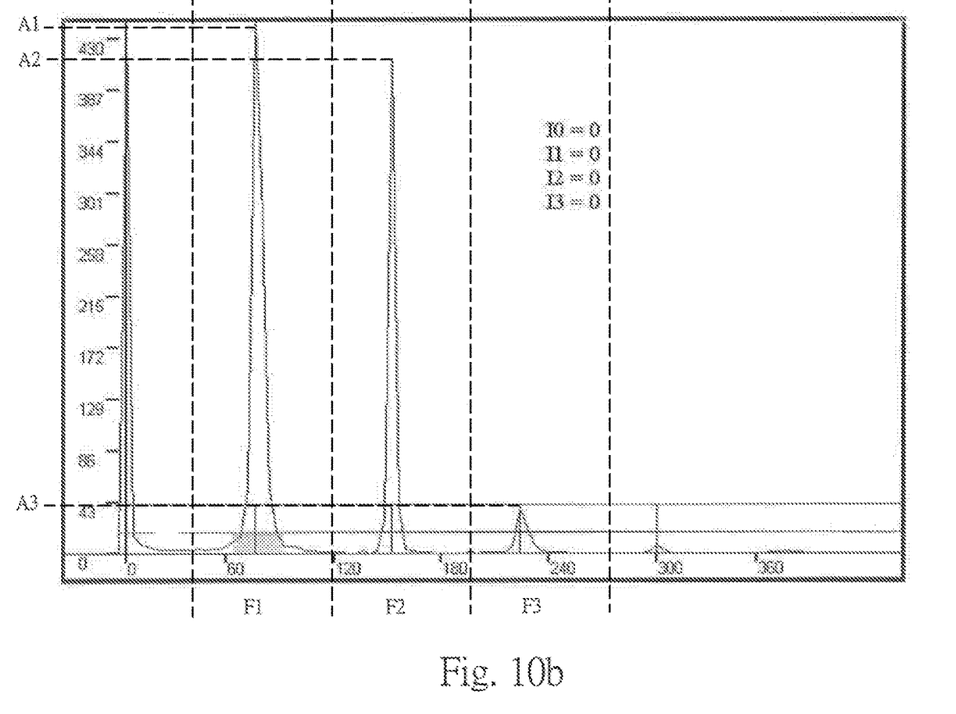
Figure 11B:
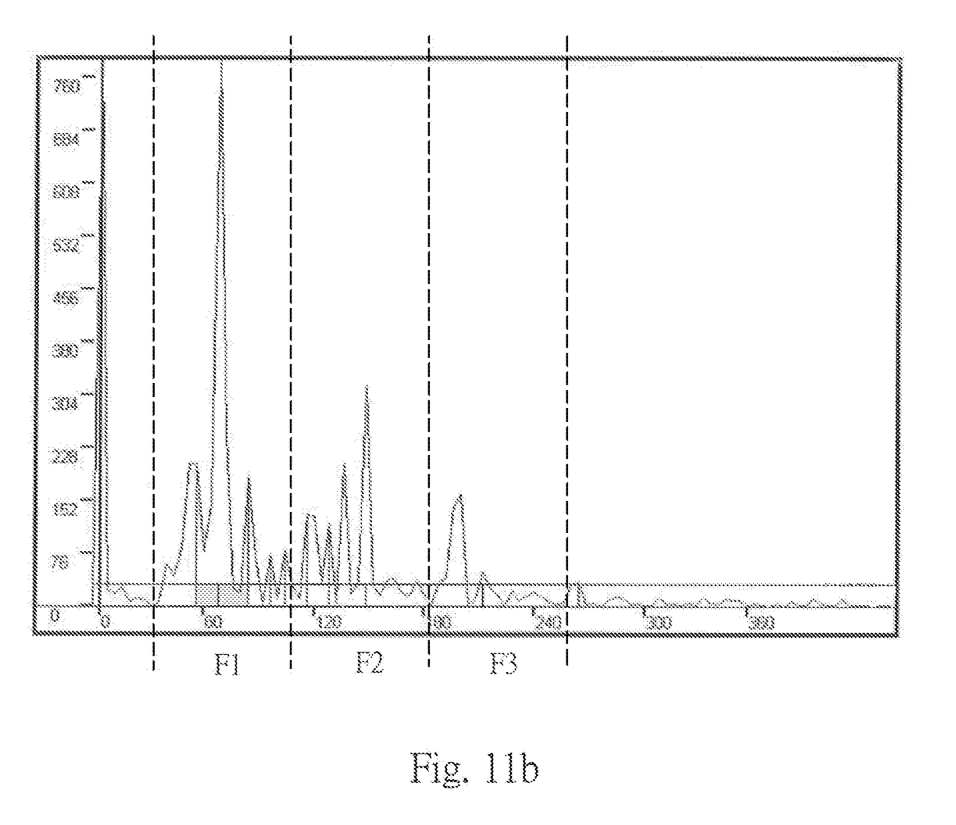

FIG. 10b and FIG. 11b respectively the energy spectrum waveforms of the pulse signals 32 in FIG. 10a and FIG. 11a, wherein the horizontal axis denotes the frequency and the vertical axis denotes the energy index (amplitude). The second module 26 converts the time pulse waveform into the energy spectrum waveform through FFT, and the frequency axis of the energy spectrum waveform includes the first frequency region F1, the second frequency region F2 and the third frequency region F3. Suppose that the proportional coefficient is 1/20. Hence, the first standard value is 5, and the second standard value is 2. Refer to FIG. 10b again. The first heart index I1, the second heart index I2 and the third heart index I3 of an ordinary testee free of cardiac arrhythmia are all zero. In FIG. 11b, the first heart index I1, the second heart index I2 and the third heart index I3 are respectively 4, 2, and 0. Thus, I1+I2+I3≥5 and I1≥2. Therefore, the testee of FIG. 11a and FIG. 11b is determined to have the possibility of atrial fibrillation.

The first, second and third measurement modes are different in the pressures applied to the arm, which are respectively in a pressure-released state, a constant average blood pressure, and a constant pressure. The conversion of the pulse signal, the analysis of the energy spectrum waveform, the calculation of the number of the noise peaks, and the definition of the heart index are identical or almost identical for the first, second and third measurement modes.

Figure 12:
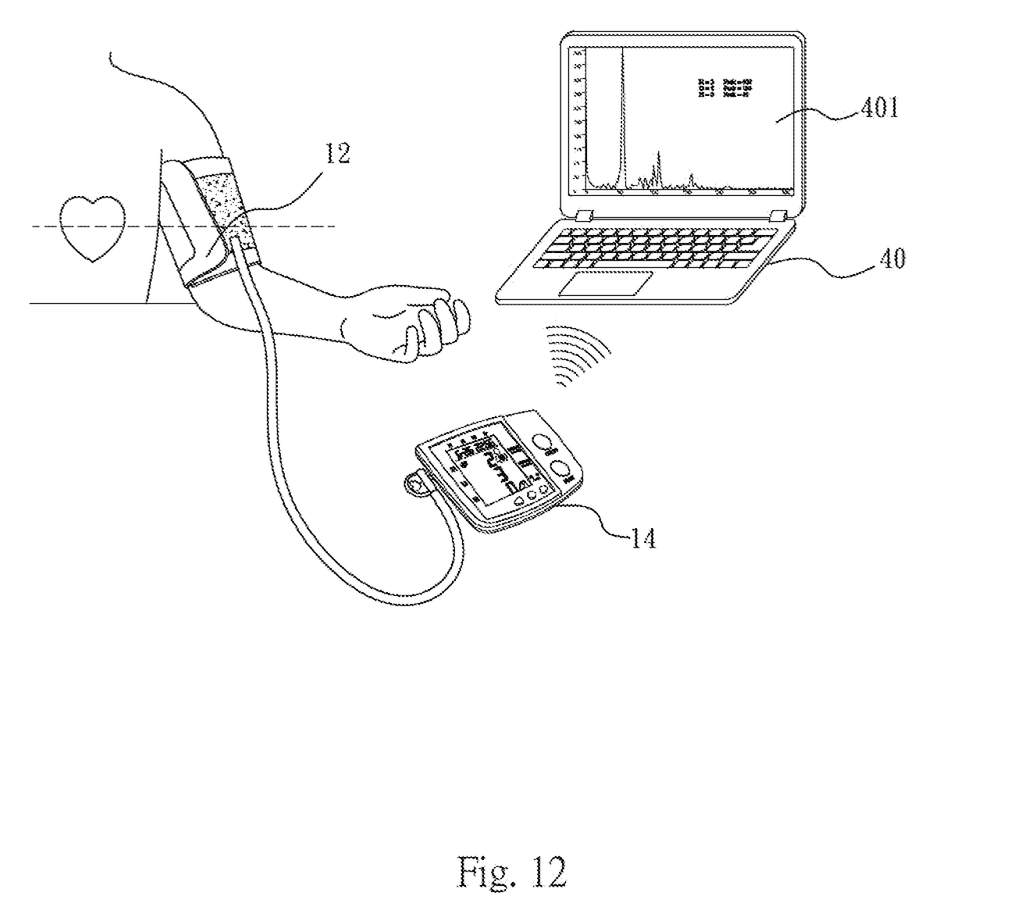
FIG. 12 is a diagram schematically showing an application of an atrial fibrillation detection apparatus according to one embodiment of the present invention.
Figure 13A:
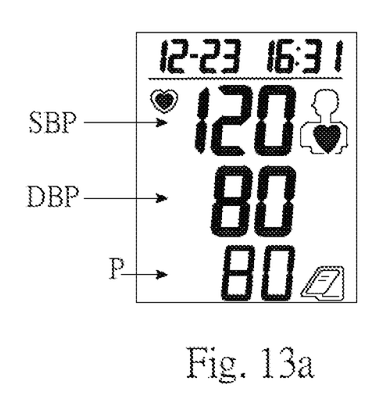
FIG. 13a and FIG. 13b are diagrams schematically showing pictures presented by a display module of an atrial fibrillation detection apparatus according to one embodiment of the present invention.
Figure 13B:
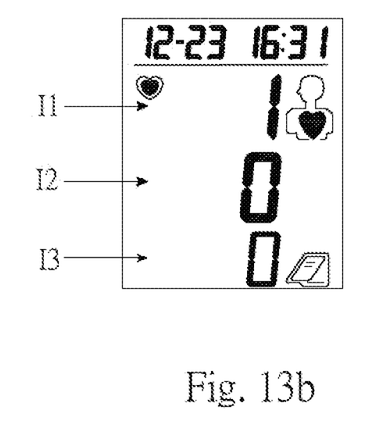

In the present invention, the first module 24, the second module 26, the third module 28, and/or the display module 30 may be integrated into a portable device 40, as shown in FIG. 12. The portable device 40 may be a mobile phone, a tablet computer, or a personal computer. The portable device 40 is in communication connection with the host device 14 in a wire or wireless method. The wireless method may be a method based on the Bluetooth technology, the Bluetooth low energy (BLE) technology, the Wi-Fi technology, or the GPRS technology. The portable device 40 may provide the computation function for the host device 14 and presents the time pulse waveform and the energy spectrum waveform on the screen 401 thereof. In one embodiment, the display module 30 of the host device 14 can alternately present two pictures, such as the picture of FIG. 13a showing the systolic blood pressure (SBP), the diastolic blood pressure (DBP) and the heartbeat (P); and the picture of FIG. 13b showing the heart indexes I1, I2 and I3. However, the present invention is not limited by the abovementioned embodiment. In one embodiment, the host device 14 has high-level computation ability and high-level display function; the first module 24, the second module 26 and the third module 28 are integrated into a control chip of the host device 14; the display module 30 presents the time pulse waveform and the energy spectrum waveform.

In one embodiment, the first module 24, the second module 26 and the third module 28 are integrated in a cloud server, and the host device 14 uploads the measurement data to the cloud server; the cloud server undertakes computation, analyzation and big-data statistics and presents the acquired heart indexes on the display module of the host device 14.

The abovementioned three measurement modes may be integrated into the control chip of a single host device 14 or respectively built in different host devices 14. The function keys 22 shown in FIG. 5 includes a setting key 221, a right selection key 222 and a left selection key 223. The user may press the setting key 221 to select the setting items established in the host device 14, such as the items for setting date, time, measurement modes, constant pressure, the first time interval, the second time interval, etc. The user may use the right selection key 222 and a left selection key 223 to assist in the setting operation. In one embodiment, the back of the host device 14 has a power connection port (not shown in the drawings) for connecting with a power cord and an electronic device connection port (not shown in the drawings) for connecting with an external portable device.

The present invention is used to determine the possibility of atrial fibrillation. The present invention can enable the user to pre-diagnose atrial fibrillation in the measurement of blood pressure, blood oxygen, or heart rate at home. Once pre-diagnosed to have the possibility of atrial fibrillation, the user is sent to a hospital for definite diagnosis and then treated professionally by physicians, whereby to prevent from apoplexy induced by atrial fibrillation. Further, the present invention can upload/store the measurement data to a portable device/cloud server, whereby the data can be used to assist in far-end healthcare.

Although the present invention has been explained in relation to its preferred embodiment, it is to be understood that other modifications and variation can be made without departing the spirit and scope of the invention as hereafter claimed.

What is claimed is:

1. An atrial fibrillation detection method comprising:
    detecting a pulse signal of a testee to obtain a time pulse waveform;
    converting the time pulse waveform into an energy spectrum waveform via Fast Fourier Transform (FFT), wherein the energy spectrum waveform includes at least three frequency regions, which are respectively a first frequency region, a second frequency region and a third frequency region, and wherein three frequency regions respectively have three primary amplitudes, which are a first primary amplitude, a second primary amplitude and a third primary amplitude;
    calculating a number of peaks of noise in each frequency region and defining the number of the peaks as a heart index of the frequency region, wherein the heart indexes of the first frequency region, the second frequency region and the third frequency region are respectively a first heart index, a second heart index and a third heart index, and wherein the primary amplitude of each frequency region is multiplied by a proportional coefficient to function as a benchmark value in the frequency region, and wherein noise signals in each frequency region, which have an intensity higher than the benchmark value, are regarded as the peaks in the frequency region; and
    using a sum of the first heart index, the second heart index and the third heart index as a judgement index and determining that there is possibility of atrial fibrillation while the judgement index is equal to or greater than a first standard value and the first heart index is equal to or greater than a second standard, wherein determination of the first standard value and the second standard value correlates with determination of the proportional coefficient.

2. The atrial fibrillation detection method according to claim 1, wherein the step of detecting a pulse signal of a testee includes steps:
    wrapping an arm of the testee with a cuff for blood pressure measurement; and
    inflating the cuff to a maximal pressure, and releasing a pressure of the cuff in a first time interval to acquire the pulse signal of the first time interval.

3. The atrial fibrillation detection method according to claim 1, wherein the step of detecting a pulse signal of a testee includes steps:
    wrapping an arm of the testee with a cuff for blood pressure measurement, inflating the cuff to a maximal pressure, and releasing a pressure of the cuff in a first time interval to acquire a systolic blood pressure (SBP) and a diastolic blood pressure (DBP);
    calculating an average blood pressure, which is equal to one-third the systolic blood pressure plus two-thirds diastolic blood pressure; and
    inflating the cuff to a constant pressure of the average blood pressure and maintain the constant pressure for a second time interval to acquire the pulse signal of the second time interval.

4. The atrial fibrillation detection method according to claim 1, wherein the step of detecting a pulse signal of a testee includes steps:
    wrapping an arm of the testee with a cuff for blood pressure measurement; and
    letting the cuff contract to apply a constant pressure to the arm for a third time interval to acquire the pulse signal of the third time interval.

5. The atrial fibrillation detection method according to claim 4, wherein the constant pressure is 50 mmHg, 60 mmHg, or 70 mmHg, or within a range of 40-70 mmHg.

6. The atrial fibrillation detection method according to claim 1 further comprising a step: transmitting one or both of the time pulse waveform and the energy spectrum waveform to a cloud server, wherein the cloud server calculates the heart indexes and provides far-end display, far-end computation, and far-end big data-statistics.

7. The atrial fibrillation detection method according to claim 1, wherein the proportional coefficient is 1/20, and the first standard value is 5, and the second standard value is 2, and wherein the 1/20 of the primary amplitude is the benchmark value, and wherein the noise signals in each frequency region, which have an intensity higher than the benchmark value, are regarded as the peaks in the frequency region, and wherein while a sum of all the heart indexes is greater than or equal to 5 and the first heart index is greater than 2, the testee is determined to has a possibility of atrial fibrillation.

8. The atrial fibrillation detection method according to claim 1, wherein the pulse signal of the testee is detected with a blood pressure measurement device, a blood oxygen measurement device, an electrocardiographic measurement device, an infrared measurement device, or a heart rate measurement device.

9. An atrial fibrillation detection apparatus comprising:
    a cuff used in blood pressure measurement, wrapping an arm of a testee, and inflated to apply a pressure to the arm to detect a pulse signal;
    a host device having a transducer thereinside, connected with the cuff through an air hose, and controlling an operation mode of the cuff to acquire a corresponding pulse signal;
    a first module acquiring a time pulse waveform of the pulse signal of the testee in a first time interval;
    a second module converting the time pulse waveform into an energy spectrum waveform through Fast Fourier Transform (FFT), wherein the energy spectrum waveform includes at least three frequency regions, which are respectively a first frequency region, a second frequency region and a third frequency region, and wherein three frequency regions respectively have three primary amplitudes, which are a first primary amplitude, a second primary amplitude and a third primary amplitude;
    a third module calculating a number of peaks of noise in each frequency region and defining the number of the peaks in each frequency region as a heart index in the frequency region, wherein the heart indexes of the first frequency region, the second frequency region and the third frequency region are respectively a first heart index, a second heart index and a third heart index, and wherein the primary amplitude of each frequency region is multiplied by a proportional coefficient to function as a benchmark value in the frequency region, and wherein noise signals in each frequency region, which have an intensity higher than the benchmark value, are regarded as the peaks in the frequency region; and a display module presenting the three heart indexes corresponding to the three frequency regions, wherein a sum of the three heart indexes and the first heart index are used to determine whether the testee has a possibility of atrial fibrillation.

10. The atrial fibrillation detection apparatus according to claim 9 further comprising a fourth module summing up all the first heart indexes to obtain a judgement index, wherein while the judgement index is equal to or greater than a first standard value and the first heart index is equal to or greater than a second standard, the testee is determined to have a possibility of atrial fibrillation, and wherein determination of the first standard value and the second standard value correlates with determination of the proportional coefficient.

11. The atrial fibrillation detection apparatus according to claim 10, wherein while the testee is determined to have a possibility of atrial fibrillation, the display module presents an alert symbol.

12. The atrial fibrillation detection apparatus according to claim 9, wherein while the host device controls the cuff to operate in a first mode, the cuff is inflated to a maximal pressure, and then the cuff releases pressure in a first time interval to acquire the pulse signal of the first time interval.

13. The atrial fibrillation detection apparatus according to claim 9, wherein while the host device controls the cuff to operate in a second mode, the cuff is inflated to a maximal pressure; next, the cuff releases pressure in a first time interval to acquire a systolic blood pressure (SBP) and a diastolic blood pressure (DBP); next is calculated an average blood pressure, which is equal to one-third the systolic blood pressure plus two-thirds diastolic blood pressure; then, the cuff is inflated to a constant pressure of the average blood pressure and maintain the constant pressure for a second time interval to acquire the pulse signal of the second time interval.

14. The atrial fibrillation detection apparatus according to claim 9, wherein while the host device controls the cuff to operate in a third mode, let the cuff contract to apply a constant pressure to the arm for a third time interval to acquire the pulse signal of the third time interval.

15. The atrial fibrillation detection apparatus according to claim 14, wherein the constant pressure is 50 mmHg, 60 mmHg, or 70 mmHg, or within a range of 40-70 mmHg.

16. The atrial fibrillation detection apparatus according to claim 9, wherein the first module, the second module, the third module, and/or the display module are integrated into a portable device, and wherein the portable device is in communication connection with the host device.

17. The atrial fibrillation detection apparatus according to claim 9, wherein the first module, the second module, the third module, and/or the display module are integrated into the host device.

18. The atrial fibrillation detection apparatus according to claim 9, wherein the first module, the second module, the third module, and/or the display module are integrated into a cloud server, and wherein the host device uploads measurement data to the cloud server.

* * * * *